United States Patent [19]

Attermeier et al.

[11] Patent Number: 5,531,711

[45] Date of Patent: * Jul. 2, 1996

[54] SAFETY CANNULA

[75] Inventors: Kurt Attermeier, Spring Grove; Thomas E. Dudar, Palatine, both of Ill.; Mark A. Stiehl, Rochester, N.Y.; Joseph M. Tartaglia, Los Altos, Calif.

[73] Assignees: Sterling Winthrop, Inc., New York, N.Y.; Baxter International, Inc., Deerfield, Ill.

[*] Notice: The term of this patent shall not extend beyond the expiration date of Pat. No. 5,389,086.

[21] Appl. No.: 376,727

[22] Filed: Jan. 23, 1995

Related U.S. Application Data

[63] Continuation of Ser. No. 909,546, Jul. 6, 1992, Pat. No. 5,389,086.

[51] Int. Cl.⁶ .................................................. A61M 5/00
[52] U.S. Cl. .......................... 604/242; 604/240; 604/905
[58] Field of Search ................................ 604/201, 203, 604/205, 232, 235, 240, 243, 905, 221, 68, 72

[56] References Cited

U.S. PATENT DOCUMENTS

| | | |
|---|---|---|
| D. 321,250 | 10/1991 | Jepson et al. . |
| D. 321,251 | 10/1991 | Jepson et al. . |
| D. 321,252 | 10/1991 | Jepson et al. . |
| D. 327,318 | 6/1992 | Dudar et al. . |
| 3,848,593 | 11/1974 | Baldwin .................................. 604/242 |
| 4,329,989 | 3/1982 | Dallons et al. . |
| 4,585,445 | 4/1986 | Hadtke . |
| 4,624,393 | 11/1986 | Lopez ..................................... 604/240 |
| 4,643,724 | 2/1987 | Jobe . |
| 4,675,020 | 6/1987 | McPhee . |
| 4,834,152 | 5/1989 | Howson .................................. 604/905 |
| 5,059,172 | 10/1991 | Sutherland . |
| 5,066,287 | 11/1991 | Ryan ...................................... 604/240 |
| 5,071,413 | 12/1991 | Utterberg ................................ 604/283 |
| 5,135,489 | 8/1992 | Jepson et al. . |
| 5,171,234 | 12/1992 | Jepson .................................... 604/283 |
| 5,226,900 | 7/1993 | Bancsi et al. . |
| 5,389,086 | 2/1995 | Attermeier ............................. 604/242 |

FOREIGN PATENT DOCUMENTS

| | | |
|---|---|---|
| 0548632 | 9/1957 | Italy ....................................... 604/240 |
| 8900273 | 10/1989 | WIPO . |
| 9006071 | 1/1990 | WIPO . |
| 9001350 | 3/1990 | WIPO . |

OTHER PUBLICATIONS

PR Newswire, "Sterling Winthrop Announces Sanofi Winthrop Licensing . . ." Corporate Library/Current News, p. 1.

*Primary Examiner*—C. Fred Rosenbaum
*Assistant Examiner*—Chalin Smith
*Attorney, Agent, or Firm*—William J. Davis

[57] ABSTRACT

A coupling system for transferring fluids from a medicament-containing cartridge to an injection site comprises a fluid flow channel, a blunt cannula defining the distal end of the fluid flow channel, a needle cannula defining the proximal end of the fluid flow channel, and means for fixedly connecting the needle cannula to the blunt cannula.

11 Claims, 4 Drawing Sheets

SAFETY CANNULA

This application is a continuation of U.S. application Ser. No. 07/909,546, filed Jul. 6, 1992, now U.S. Pat. No. 5,389,086.

BACKGROUND OF THE INVENTION

1. Field of Invention

This invention relates to coupling systems for transferring materials from one flow conduit to another.

2. Description of the Prior Art

Disposable medicament-containing cartridge-needle units for use in conjunction with reusable hypodermic syringe holders are well known in the art. Such cartridges conventionally feature a cylindrical body closed at the proximal end with a flexible piston slidable within the bore of the cartridge and closed at the distal necked-down end with a diaphragm secured to the cartridge by a crimped-on metal collar. The necked-down distal end conventionally is fitted with a steel needle/needle hub unit and a needle sheath. Such needle/needle hub units have, minimally, a sharp end, typical of the type associated with hypodermic syringes.

Such cartridge-needle units can be used in conjunction with reusable syringe holders which allow the user to avoid handling the cartridge-needle unit when the needle is exposed. Nevertheless, health care workers are especially susceptible to accidental and potentially infectious, and indeed, on occasion, possibly fatal, needle strikes due to the careless handling and/or disposing of the cartridge-needle unit after use. The consequences to health care workers of strikes from needles contaminated with various infectious diseases such as hepatitis or AIDS can be particularly severe. The frequency of such accidental needle strikes in the United States is surprisingly great, and has been estimated to be approximately one million needle strikes per year. Moreover, the cost to health care organizations for the testing of health care workers accidentally stricken by used needles is a significant burden on health care costs. Therefore, it would be desirable to further protect health care workers by providing medicament containing cartridges without having to expose the user to the needle commonly associated with such cartridges.

In response to the "accidental needle strike" situation, numerous devices have been developed which typically shield or cover the sharp needle tip. One recently developed system, as described in PCT/US89/00273, comprises a preslit injection site specifically designed to receive a blunt cannula. Commercially available under the InterLink trademark, this pre-slit injection site and blunt cannula have been adapted for intravenous administration as described in pending U.S. and foreign patent applications. One of the key features of this system is the elimination of traditional "sharp" needles which are used in numerous procedures. For example, as described in PCT/US90/01350, the blunt cannula device is depicted in a press-fit combination with a syringe of known construction. Rather than using a traditional needle, the blunt cannula device is attached to the syringe and then inserted through the pre-slit injection site located in an IV tubing line. The content of the syringe is then delivered into the IV line. Once the content is delivered, the cannula is withdrawn from the site and properly disposed. Hence, the administration of the syringe content, through an IV line, can now be completed without the use of a standard needle.

Hence, it would be highly desirable to provide conventional disposable medicament cartridges adaptable to such blunt cannulae and useable with such pre-slit injection sites.

SUMMARY OF THE INVENTION

In accordance with this invention, an improved coupling system is provided for transferring fluids from a medicament-containing cartridge to an injection site which reduces the possibility of accidental needle strikes.

More specifically, this invention provides an improved coupling system for transferring fluids from a medicament-containing cartridge to a pre-slit injection site, the coupling system comprising a fluid flow channel, a blunt cannula defining the distal end of the fluid flow channel, a needle cannula defining the proximal end of the fluid flow channel, and means for fixedly connecting the needle cannula to the blunt cannula. In a preferred embodiment, the coupling system includes a hub comprising the blunt cannula and a sleeve portion which extends around and beyond the proximal end of the needle cannula.

It is an advantageous feature of this invention that an improved coupling system is provided for commercially available medicament-containing cartridges which can be used safely and effectively without exposing the user to the needle cannula. This reduces the susceptibility of health care workers to accidental needle strikes.

It is another advantageous feature of this invention that a safety coupling device is provided that may not be subject to a potentially lengthy approval process before the U.S. Food and Drug Administration.

Other advantages will become readily apparent upon reference to the following description of preferred embodiments when read in light of the accompanying drawings.

DESCRIPTION OF PREFERRED EMBODIMENTS

Figure 1:
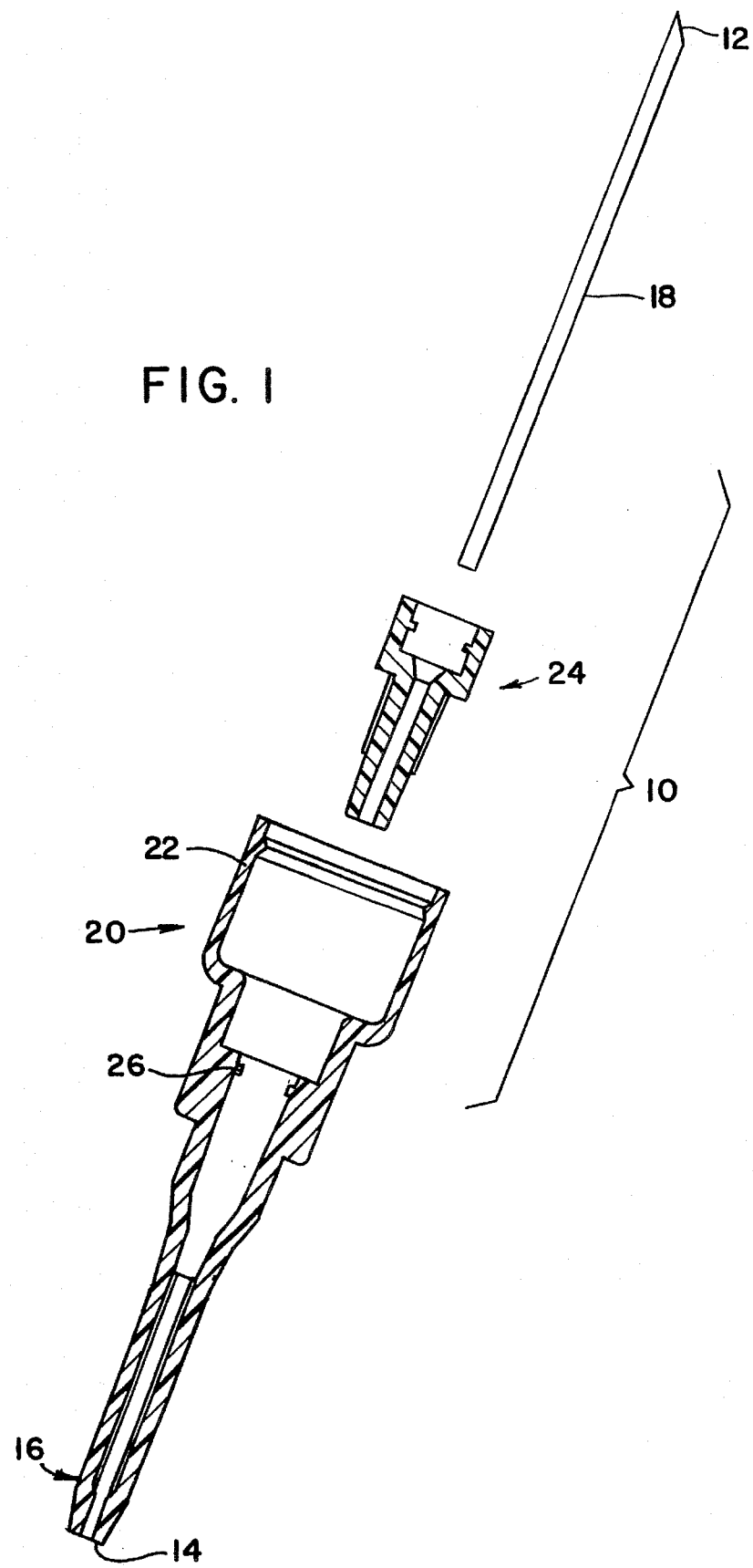
FIG. 1 is an exploded cross-section showing a preferred embodiment of the coupling system of this invention.

While this invention is described hereinafter particularly with respect to a preferred embodiment, i.e., a coupling system for transferring fluids from a medicament-containing cartridge to a pre-slit injection site, it also finds utility in other coupling systems for transferring fluid materials from one flow conduit to another.

With reference to the drawings, a coupling system of this invention, represented by 10, is intended for use in combination with a conventional disposable medicament-containing cartridge. The coupling system includes a fluid flow channel, having a proximal end 12 and a distal end 14, a blunt cannula 16 defining the distal end of the fluid flow channel, a needle cannula 18 defining the proximal end of the fluid flow channel, and means described hereinafter for fixedly connecting the needle cannula to the blunt cannula.

In a preferred embodiment, the coupling system comprises a hub 20 comprising the blunt cannula 16 defining the distal end of the fluid flow channel and a sleeve portion 22 which extends around and beyond the proximal end of the needle cannula when assembled. It is possible to assemble the coupling system at the manufacturer's site, thereby virtually eliminating user exposure to needle cannula 12.

Needle cannula 12 can be a single or double sharp ended needle cannula of the type commonly associated with hypodermic syringes. A needle cannula of the single ended type, as shown in FIG. 1, is preferred. The needle cannula preferably is fabricated of stainless steel.

For use with conventional cartridges, e.g., commercially available Carpuject™ sterile cartridges, the radius r of sleeve 22 is about 5 mm and the distance x between the end of sleeve 22 and the proximal end of needle cannula 18 preferably is at least about 2 mm, more preferably 3 mm, so that the proximal end of the needle cannula is adequately shielded when the coupling system is not attached to the cartridge. The distal end of the needle cannula 18 can be flush with the distal end of the blunt cannula. However, to reduce the undesirable possibility of the needle cannula extending beyond the distal end of the blunt cannula due to manufacturing tolerances, a clearance Y of at least about 0.5 mm, and preferably, of about 1 mm can be provided.

Blunt cannula 16 is tapered at its distal end to engage an injection site. The blunt cannula 16 preferably is an integral part of hub 20. The specifics of the design of the tapered blunt cannula end portion of hub 20 can be ascertained with reference to PCT/US89/000273, PCT/US90/01350, and other pending applications, the disclosures of which are hereby incorporated by reference, which describe tapered blunt cannulae for use with pre-slit injection sites.

Various means can be employed for fixedly connecting the needle cannula to the blunt cannula and/or the hub comprising the blunt cannula. For example, the fluid flow path inside the blunt cannula can be tapered such that the needle cannula can be inserted into and adhesively connected to the blunt cannula. Suitable adhesives include, e.g., an epoxy based resin, and can be applied to the outside surface of the needle cannula prior to insertion into the hub. Alternatively, the needle cannula can be inserted into the blunt cannula or hub and the blunt cannula or hub can be melted or welded to connect the needle cannula to the blunt cannula. In another embodiment, the connecting means can take the form of an insert 24 which can be sized to fit through sleeve 22 and snap into mating portion 26 in the middle section of hub 20.

A removable cover sheath 28 can be provided to surround blunt cannula 16 during storage and handling to preserve the sterility of the cannula. Cover sheath 28 can be snapped into engagement with the hub to surround and protect the outwardly projecting distal end of blunt cannula 16.

Disposable medication cartridge 30 is of a conventional design and includes a hollow, transparent body which is prefilled with a supply of fluid medication or the like. Such cartridges currently are in widespread commercial use. Cartridge 30 includes a head 32 and a cylindrical body 34 which are coextensively joined together at a relatively narrow neck 36. A metallic end cap 38 covers a sealed diaphragm 40 which extends across cartridge 30 to prevent contamination and leakage of the fluid contents. A piston 42 is sized to be received in and slidable axially and reciprocally through the interior of cartridge 30. Piston 42 is formed from a relatively dense resilient material, e.g., rubber, and can be moved distally through cartridge 30 for expulsing the fluid contents of the cartridge via the needle cannula 18. A screw-threaded rod 44 can be connected to the piston 42 so as to project outwardly from the end of piston 42. Screw-threaded rod 44 can be mated to a screw-threaded piston stem of an associated holder to complete a piston assembly for controlling the movement of piston 42 through the interior of cartridge 30. It is contemplated that other means known in the art can be employed for attaching the rod to the piston stem.

The above-described medicament-containing cartridges are designed for use in conjunction with reusable or other disposable syringe holders. Exemplary useful syringe holders are described, for example, in Hadtke, U.S. Pat. No. 4,585,445 and EPO 485,028 the disclosures of which are hereby incorporated by reference.

Figure 4:
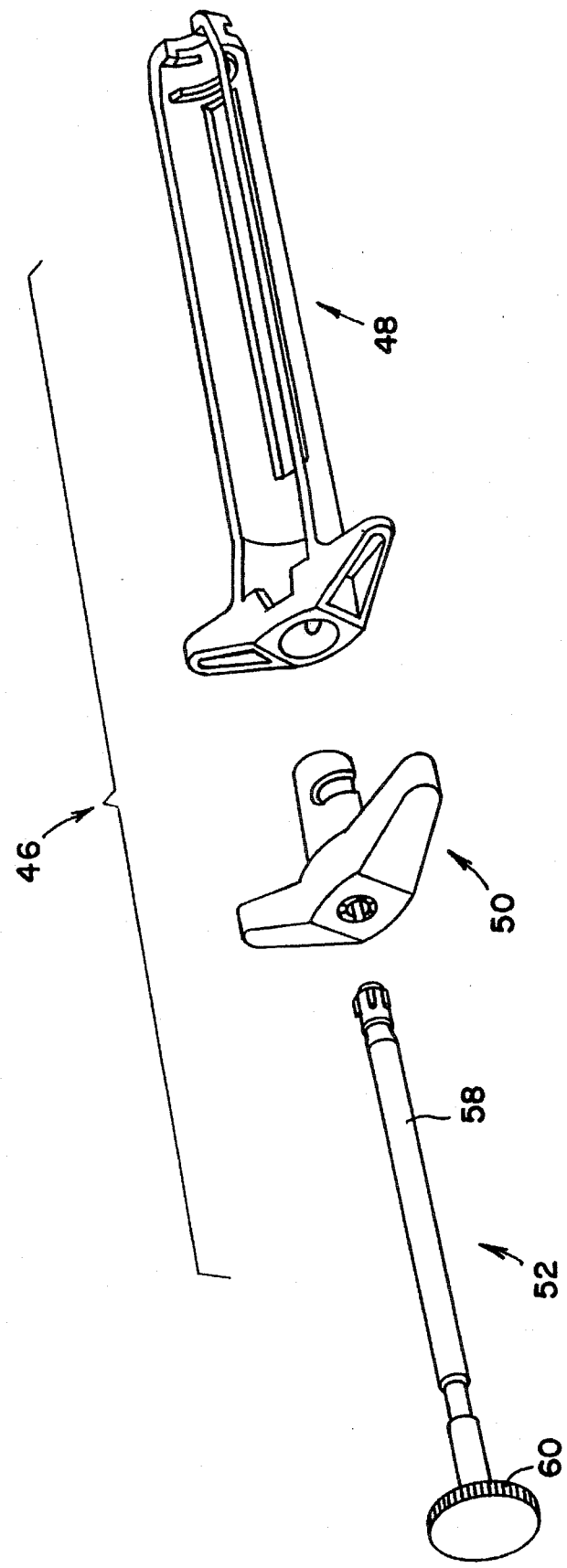
FIG. 4 is an exploded view of a syringe holder which can be used in conjunction with the coupling system-cartridge combination of this invention.

Such a syringe holder 46 as depicted in FIG. 4, can comprise a cylindrical frame 48, a clamp 50, and a plunger element 52 containing a piston stem 58.

Figure 2:
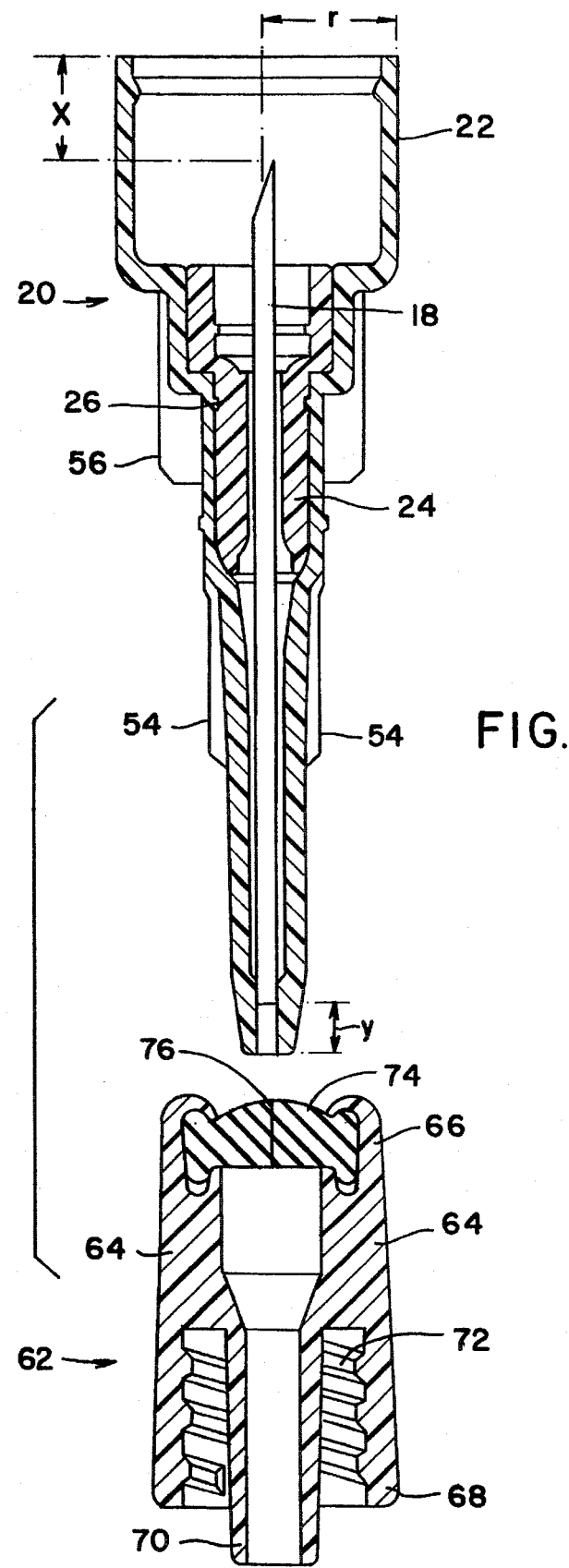
FIG. 2 is a cross-section showing a coupling system of this invention in an assembled relation and a pre-slit injection site.
Figure 3:
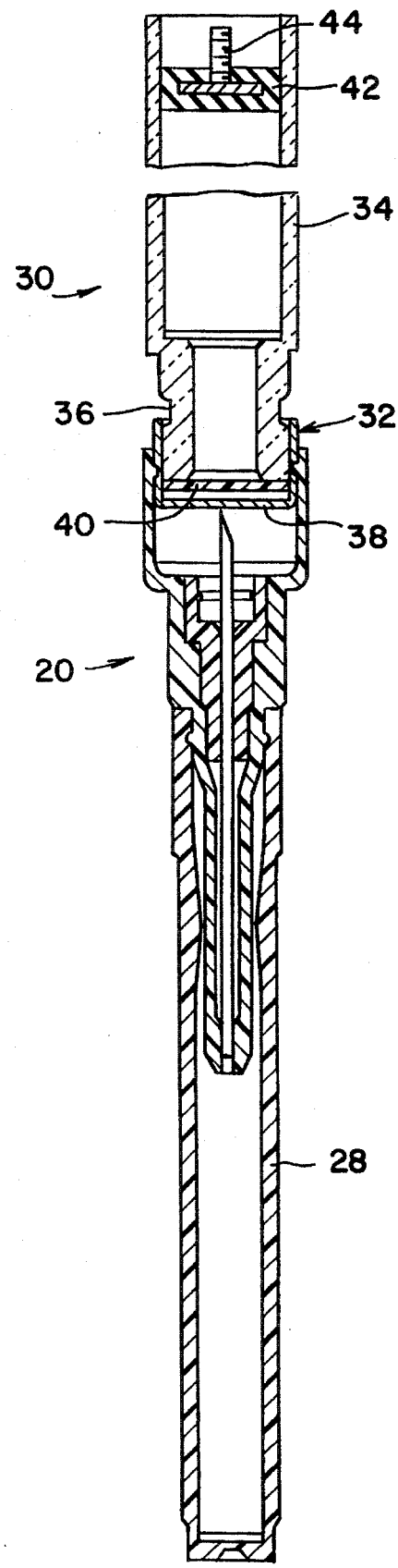
FIG. 3 shows in cross-section a coupling system of this invention in combination with a conventional medication-containing cartridge.

In preferred embodiments, the coupling system of this invention is practiced in conjunction with a pre-slit injection site as described in PCT/US89/00273, PCT/US90/01350 and depicted in FIG. 2. Injection site 62 has a cylindrical housing 64, a first end 66, a second end 68, and a hollow cylindrical fluid flow member 70 which can slidably engage a receiving member, e.g., the housing of a catheter, thereby providing a sterile fluid flow coupling. Internal male luer threads 72, shown to be carried by housing 64 to adjacent the second end 68, engage a flange member (not illustrated) when the injection site is rotated. The injection site 62 contains a resealable septum 74 formed of, for example, a latex, synthetic rubber or thermoplastic elastomer. The septum 74 has either a partial or complete opening or slit 76.

The hub 20 preferably is attachable to the cartridge by snapping sleeve portion 22 over the distal end of the cartridge to engage the metal cap 38. In order to obtain the requisite sterile seal and flexibility, the hub preferably is fabricated of a plastic material such as polyethylene or polypropylene, or a polypropylene copolymer containing a minor amount of, e.g., low density polyethylene, to increase the impact strength of the polymer. An example of the latter copolymer is Pro-fax 8523, available from Himont Incorporated. Such copolymer is particularly preferred when the hub is prepared by conventional injection molding techniques.

The hub 20 can be optionally provided with a first set of fins 54 at the base of the blunt cannula for manufacturing purposes. Such fins may also provide a sense of resistance alerting the user, to prevent the cannula 16 and/or hub 20 from being penetrated too deeply into the port of an injection site as shown in FIG. 2. The hub can optionally be provided with a second set of fins 56 at the base of the sleeve to provide a stop for the blunt cannula sheath.

The coupling system 10 of this invention can be prepared by inserting a needle cannula 18 through the insert 24. The insert 24 is preferably fabricated of an injection moldable plastic, e.g., polycarbonate or polypropylene, and can be pre-sterilized or pre-treated for improved adhesion, e.g., by corona discharge treatment. An adhesive, e.g., a UV curable epoxy resin, can be applied to the needle/insert interface and, subsequently, the resin can be cured. The coupling system 10 preferably is sterlizable such as by means of radiation, steam or ethylene oxide. The needle cannula-insert subassembly can then be press fit through the sleeve 22 into the hub 20. The sheath 28 can then be fitted over the hub 20, and the coupling system-sheath subassembly can be snap fitted over the necked down end of the cartridge 30.

In use, the coupling system 10 of this invention operates in conjunction with conventional medicament-containing cartridges, reusable syringe holders and injection sites during and after administration of an injection as follows. In the injection state, the prefilled medication cartridge 30 fitted with the coupling system 10 of this invention is loaded into cylindrical frame 48 of an assembled reusable syringe holder 46 such as described above so that blunt cannula 16 covered by sheath 28 extends distally outward from the frame. Cartridge 30 is then advanced by a health care worker distally through the holder by rotating clamping element 50 until the inwardly extending proximal end of needle cannula 12 penetrates sealed diaphragm 40 of cartridge 30.

Next, sheath 28 is removed to expose the outwardly extending distal end of blunt cannula 16. A screw threaded piston stem 58 is connected to piston 42 at the screw-threaded rod 44 thereof. The blunt cannula 16 is inserted into a pre-slit injection site, such as described above, and an axially and distally directed force is applied by the health care worker to piston stem 52, via actuation button 60. The distal force is transferred from piston stem 58 to piston 44 to drive the piston through medicament-containing cartridge 30 and thereby expulse the fluid contents of the cartridge 30 via needle cannula 18 through the fluid flow channel and into the fluid flow member 70 of the pre-slit injection site 62. After injection, the blunt cannula 16 is removed from the injection site. Subsequently, the plunger rod 44 is unscrewed from the piston thread and pulled proximally back, the clamp 50 is rotated to free the cartridge 30 and the cartridge unit is disposed of in an appropriate manner, the needle cannula 18 being safely covered by the hub 20, sleeve 22 and/or blunt cannula 16 during the entire procedure, thus reducing the possibility of accidental needle strikes.

The invention has been described in detail with particular reference to certain preferred embodiments thereof, but it will be understood that variations and modifications can be effected within the spirit and scope of the invention.

What is claimed is:

1. A coupling system-cartridge assembly comprising in combination,
   (1) a cartridge, comprising a hollow body prefilled with a medication having a sealed diaphragm on the distal end thereof and a piston axially and reciprocally slidable through the interior of said body; and
   (2) a coupling system for transferring fluids from said cartridge to an injection site, said coupling system comprising:
   a fluid flow channel having proximal and distal ends;
   a stainless steel needle cannula defining the proximal end of said fluid flow channel; and
   a hub attached to the distal end of said cartridge comprising a blunt cannula portion defining the distal end of said fluid flow channel and a sleeve portion which extends beyond the proximal end of said needle cannula
   wherein said hub is attached to said cartridge by snapping said sleeve over the distal end of said cartridge,
   wherein said piston can be activated through said cartridge to expulse the medication contained in said cartridge through said fluid flow channel into said injection site.

2. The coupling system of claim 1 wherein the blunt cannula is fabricated of a plastic material selected from the group consisting of polyethylene, polypropylene and a polypropylene copolymer containing low density polyethylene.

3. The coupling system of claim 1 wherein the hub is fabricated of a plastic material selected from the group consisting of polyethylene, polypropylene and a polypropylene copolymer containing low density polyethylene.

4. The coupling system-cartridge assembly of claim 3 wherein the hub is fabricated of a plastic material selected from the group consisting of polyethylene, polypropylene and a polypropylene copolymer containing low density polyethylene.

5. The coupling system of claim 1 wherein the distal end of said needle cannula is approximately flush with the distal end of said blunt cannula.

6. The coupling system of claim 1 wherein the distal end of said needle cannula is approximately flush with the distal end of said blunt cannula.

7. The coupling system-cartridge assembly of claim 1 wherein the distal end of said needle cannula is approximately flush with the distal end of said blunt cannula.

8. The coupling system of claim 1 wherein the sleeve portion of said hub has a radius of about 5 mm.

9. The coupling system-cartridge assembly of claim 1 wherein the sleeve portion of said hub has a radius of about 5 mm.

10. The coupling system of claim 1 wherein the distance between the end of the sleeve and the proximal end of the needle cannula is at least 2 mm.

11. The coupling system-cartridge assembly of claim 1 wherein the distance between the end of the sleeve and the proximal end of the needle cannula is at least 2 mm.

* * * * *